United States Patent [19]

Taguchi et al.

[11] Patent Number: 5,701,575
[45] Date of Patent: Dec. 23, 1997

[54] ARTICLE MADE OF A TI-AL INTERMETALLIC COMPOUND, AND METHOD FOR FABRICATION OF SAME

[75] Inventors: Kohei Taguchi; Michihiko Ayada, both of Kanagawa-ken; Hideo Shingu, Kyotofu, all of Japan

[73] Assignee: NHK Spring Co., Ltd., Japan

[21] Appl. No.: 575,969

[22] Filed: Jan. 11, 1996

Related U.S. Application Data

[63] Continuation of Ser. No. 148,438, Nov. 8, 1993, abandoned.

[30] Foreign Application Priority Data

| Nov. 9, 1992 | [JP] | Japan | 4-322226 |
| May 13, 1993 | [JP] | Japan | 5-134180 |

[51] Int. Cl.⁶ ........................ B22F 3/16
[52] U.S. Cl. .............. 419/28; 419/2; 419/26; 419/29; 419/45; 419/46; 419/47; 419/48; 419/49; 419/58; 419/55
[58] Field of Search ............... 148/671; 419/2, 419/26, 28, 29, 45, 46, 47, 48, 49, 53, 55; 420/418; 428/614

[56] References Cited

U.S. PATENT DOCUMENTS

| 4,292,077 | 9/1981 | Blackburn et al. | 75/175.5 |
| 4,294,615 | 10/1981 | Blackburn et al. | 75/175.5 |
| 4,331,477 | 5/1982 | Kubo et al. | 75/228 |
| 4,661,316 | 4/1987 | Hashimoto et al. | 420/418 |
| 4,668,282 | 5/1987 | Gilman et al. | 75/0.5 R |
| 4,668,470 | 5/1987 | Gilman et al. | 419/32 |
| 4,716,020 | 12/1987 | Blackburn et al. | 420/418 |
| 5,045,406 | 9/1991 | Huang et al. | 428/614 |
| 5,196,162 | 3/1993 | Maki et al. | 420/418 |
| 5,205,876 | 4/1993 | Sakai | 148/421 |
| 5,226,985 | 7/1993 | Kim et al. | 148/671 |
| 5,271,844 | 12/1993 | Huang et al. | 420/418 |
| 5,350,466 | 9/1994 | Larsen, Jr. et al. | 148/421 |
| 5,409,781 | 4/1995 | Rosler et al. | 428/547 |
| 5,429,796 | 7/1995 | Larsen, Jr. | 420/590 |

FOREIGN PATENT DOCUMENTS

| 02-101133 | 4/1990 | Japan . |
| 02-250931 | 10/1990 | Japan . |
| 03-199358 | 8/1991 | Japan . |
| 4-304 | 1/1992 | Japan . |
| 4-305 | 1/1992 | Japan . |
| 04-63237 | 2/1992 | Japan . |
| 04-124236 | 4/1992 | Japan . |
| 04-304 | 4/1992 | Japan . |
| 04-305 | 4/1992 | Japan . |
| 4309 | 4/1992 | Japan | B22F 3/14 |
| 4210408 | 11/1992 | Japan | B22F 7/00 |

*Primary Examiner*—Charles T. Jordan
*Assistant Examiner*—Anthony R. Chi
*Attorney, Agent, or Firm*—Skjerven, Morrill, MacPherson, Franklin & Friel; Alan H. MacPherson; Omkar K. Suryadevara

[57] ABSTRACT

An article essentially consisting of one or more of Ti—Al intermetallic compounds is fabricated so as to have a volume ratio of voids no more than 3.5%, by preparing a mixture of materials selected from a group consisting of Ti, Ti alloys, Al, Al alloys, and Ti—Al compounds, having a composition suitable for forming a desired Ti—Al intermetallic compound, and heating said mixture so that said mixture may be sintered. Typically, the temperature and pressure for the heating or sintering process is appropriately selected so that the desired porosity may be obtained. The mechanical strength of an article according to the present invention is not only improved but is highly predictable, or, in other word, highly reliable. The fabrication costs can be reduced because the fabrication process involves only relatively low temperatures when pressing and heating the work at the same time. Furthermore, during the process of fabrication, the article may demonstrate a highly favorable workability so that the final shape can be given to the work without involving any undue difficulty.

24 Claims, 7 Drawing Sheets

ARTICLE MADE OF A TI-AL INTERMETALLIC COMPOUND, AND METHOD FOR FABRICATION OF SAME

This is a continuation of application Ser. No. 08/148,438, filed Nov. 08, 1993 now abandoned.

TECHNICAL FIELD

The present invention relates to an article made of a Ti—Al intermetallic compound, and a method for fabricating such an article.

BACKGROUND OF THE INVENTION

Ti—Al intermetallic compounds are attracting attention as a highly promising material for various applications because they are resistant to heat, acid and wear, and extremely light-weight. Typical applications of Ti—Al intermetallic compounds include outer wall members which are exposed to high temperatures, and various engine components such as turbine components, pistons, and valve systems.

According to a known method for fabricating an article made of a Ti—Al intermetallic compound, a mixture of Ti and Al powders was heated to a temperature of approximately 1,300° C. under high pressure. It is also known to carry out a heat treatment to the thus fabricated article at a lower temperature to remove stress existing in the article. Also is known the so-called self-propagation high temperature synthesis process (reaction synthesis process). According to this process, a mixture of Ti and Al powders is heated to a temperature higher than the reaction temperature so that the reaction is locally initiated. The heat resulting from the local reaction causes a chain reaction which propagates the reaction to the entire mixture so that an intermetallic compound can be obtained without melting the mixture.

It can be surmised that the ratio of the volume occupied by voids in an intermetallic compound or the porosity has a negative effect on the mechanical strength as is the case with other materials. However, the use of Ti—Al intermetallic compounds was started so recently that the relationship between the porosity and the mechanical strength has not been fully determined, and more research is needed for ensuring a high level of reliability in applying Ti—Al intermetallic compounds to various mechanical components by allowing accurate prediction of mechanical strength when the porosity is given.

When a highly dense structure is to be attained in a Ti—Al intermetallic compound, it is necessary to use a high temperature and pressure. It requires expensive special facilities and equipment to achieve such a high temperature and pressure. Furthermore, Ti—Al intermetallic compounds are known to be unsuitable for working. For instance, when a member made of a Ti—Al intermetallic compound is to be forged, an extremely high load is required to carry it out. Therefore, conventionally, it was necessary to conduct special treatments to obtain a fine crystal grain structure (less than 15 μm), and forge the material at a temperature in excess of 1000° C.

BRIEF SUMMARY OF THE INVENTION

In view of such problems of the prior art, a primary object of the present invention is to provide an article made of a Ti—Al intermetallic compound which has a high mechanical strength but does not require an extremely high pressure when forming it at a high temperature.

A second object of the present invention is to provide an article made of a Ti—Al intermetallic compound which does not require any undesirably high temperature for fabrication, and can thereby reduce the fabrication cost.

A third object of the present invention is to provide an article made of a Ti—Al intermetallic compound which does not require any expensive special facilities for its fabrication.

A fourth object of the present invention is to provide an article made of a Ti—Al intermetallic compound which has a structure suitable for working.

A fifth object of the present invention is to provide a method for fabricating an article made of a Ti—Al intermetallic compound having such favorable properties.

These and other objects of the present invention can be accomplished by providing an article essentially consisting of one or more of Ti—Al intermetallic compounds, wherein a volume ratio of voids existing in the article is no more than 3.5%. Such an article may be fabricated by a method comprising the steps of: preparing a mixture of materials selected from a group consisting of Ti, Ti alloys, Al, Al alloys, and Ti—Al compounds, having a composition suitable for forming a desired Ti—Al intermetallic compound; and heating the mixture so that the mixture may be sintered, and have a volume ratio of voids no more than 3.5%.

The Ti—Al compounds suitable as materials for carrying out the method of the present invention may consist of TiAl powder, $Ti_3Al$ powder or the like. The materials may be in various forms such as powder, foil, wire or the like. The material may be pressed into a compact during the heating step by a quasi hot isostatic process (PHIP, quasi HIP or the like) using a pressure medium such as ceramics, a hot press process (HP), or a hot isostatic process (HIP).

According to the experiments conducted by the inventors, it was found that the bending strength of Ti—Al compounds makes a marked change when the volume ratio of voids is approximately 3.5%, and a desired mechanical strength can be obtained by controlling the volume ratio of voids below 3.5%, preferably between 0.4% and 3.5%, most preferably between 1.3% and 3.5%. Material properties similar to a full density Ti—Al intermetallic compound can be obtained if the volume ratio of voids is no more than 0.5%.

According to a preferred embodiment of the present invention, to achieve such a volume ratio of voids, the heating step includes pressing of the compact while it is heated to a temperature higher than 1000° C. The pressing may be started any time between the time when the compact is still at the room temperature before it is heated and the time when the compact has heated to the final heating temperature.

Because the mechanical strength of the mixture drops sharply when the temperature rises higher than 1000° C., voids can be easily collapsed at such a temperature. In this case, a HIP can be used, but a quasi HIP produces even better results because shear stress acts upon the material due to the anisotropicity of pressure, and this promotes the collapsing of voids.

The pressure used in the heating step is desired to be high, but the pressure used in the quasi HIP according to the present invention is in the order of 350 kgf/cm². The use of a quasi HIP allows a dense structure to be obtained by using a relatively low pressure, and this is highly effective in reducing the fabrication cost.

According to a preferred embodiment of the present invention, the temperature for the heating step is higher than a temperature for melting the metallic phase of Al, and, following the heating step, a heat treatment process for diffusion is conducted at a temperature higher than the temperature for the heating process. In this case, the compact may be pressurized continually from the room temperature to the temperature high enough to melt Al. The diffusion heat treatment process may be carried out without pressurizing the mixture.

It was determined by inventors that the heating the compact to a temperature higher than the melting point of Al significantly increases the effectiveness of the diffusion heat treatment in removing pores from the structure. When the compact is heated to a temperature higher than the melting point of Al, and Al forms a liquid phase, it increases the effectiveness of pressing in removing pores, and highly dense blocks are formed. Furthermore, in these blocks, most of the metallic Al phase eventually forms compounds, and almost no metallic Al phase will remain because the reaction progresses more rapidly and compounds are formed more quickly in the liquid phase than in the solid phase. The liquid Al phase is prone to generation of voids due to the Kirkendall effect, but is rapidly eliminated by the heating process without substantially affecting the effectiveness in removing pores as a whole.

Thus, creation of an Al liquid phase is effective in forming a highly dense structure, and the heating speed is desired to be higher than 0.1° C./min. By increasing the heating speed higher than 10° C./min, a large amount of liquid phase is produced, and heat is rapidly generated so that voids are highly effectively removed. If the heating speed is less than 0.1° C./min, the reaction tends to progress before any liquid phase develops, and the liquid phase may not be generated to a sufficient degree.

In particular, because the reaction synthesis process tends to produce a large amount of gas from the surface of the compact due to the rapid temperature rise, the use of a quasi HIP is effective. Because a quasi HIP normally uses ceramics as a medium for pressurization, the produced gas can be vented from the gaps between the ceramics particles. Thus, a quasi HIP allows the generated gas to escape while pressing a compact molded into a complex shape, and promotes removal of pores. It is also possible to create a vacuum environment or other gas environment while pressing the mixture with ceramic powder. This applies equally to the case where intermetallic compounds are used as the starting material.

When pure Al is used, the heating temperature would then be 660° C., but the temperature may vary depending on the kind of elements which may be added to Al. As such elements, for instance, there are boron (B), manganese (Mn), tin (Sn) and nickel (Ni).

It is also possible to form an intermetallic compound by solid phase diffusion even at a temperature below the melting point of Al. In this case, a small amount of metallic Al phase may remain in the structure, and this will reduce the reliability of the product. Therefore, it is desirable to use a temperature higher than the melting point of Al. By the intervention of the liquid phase of Al, pores are effectively removed, and the effect of pressing is improved. In particular, open pores which are connected to the surface can be readily removed, and even closed pores can be readily removed by diffusion during a heat treatment process. Thus, the volume ratio of voids can be effectively reduced below 3.5% by the heat treatment process.

The γ phase mentioned in this disclosure mainly consists of fine crystals of TiAl, but may contain small amounts of $Al_3Ti$ and $Ti_3Al$. The $\alpha_2$ phase mainly consists of fine crystals of $Ti_3Al$, but may contain small amounts of TiAl and metallic Ti. The lamella structure consists of alternating layers of TiAl and $Ti_3Al$, and is substantially homogeneous. The γ phase and the lamella structure are more resistant to heat than the $\alpha_2$ phase, and are therefore more preferable as a heat resistant, light-weight material.

The range of composition suitable for obtaining a structure essentially consisting of Ti—Al intermetallic compounds is Ti:Al=83:17 to 10:90 ($_{at}\%$), and the range of composition suitable for obtaining a lamella structure is 65:35 to 50:50 ($_{at}\%$). These figures may vary depending on the amounts and kinds of alloy elements which may be added.

BRIEF DESCRIPTION OF THE DRAWINGS

Now the present invention is described in the following with reference to the appended drawings, in which.

DETAILED DESCRIPTION OF THE PREFERRED EMBODIMENTS

Figure 1:
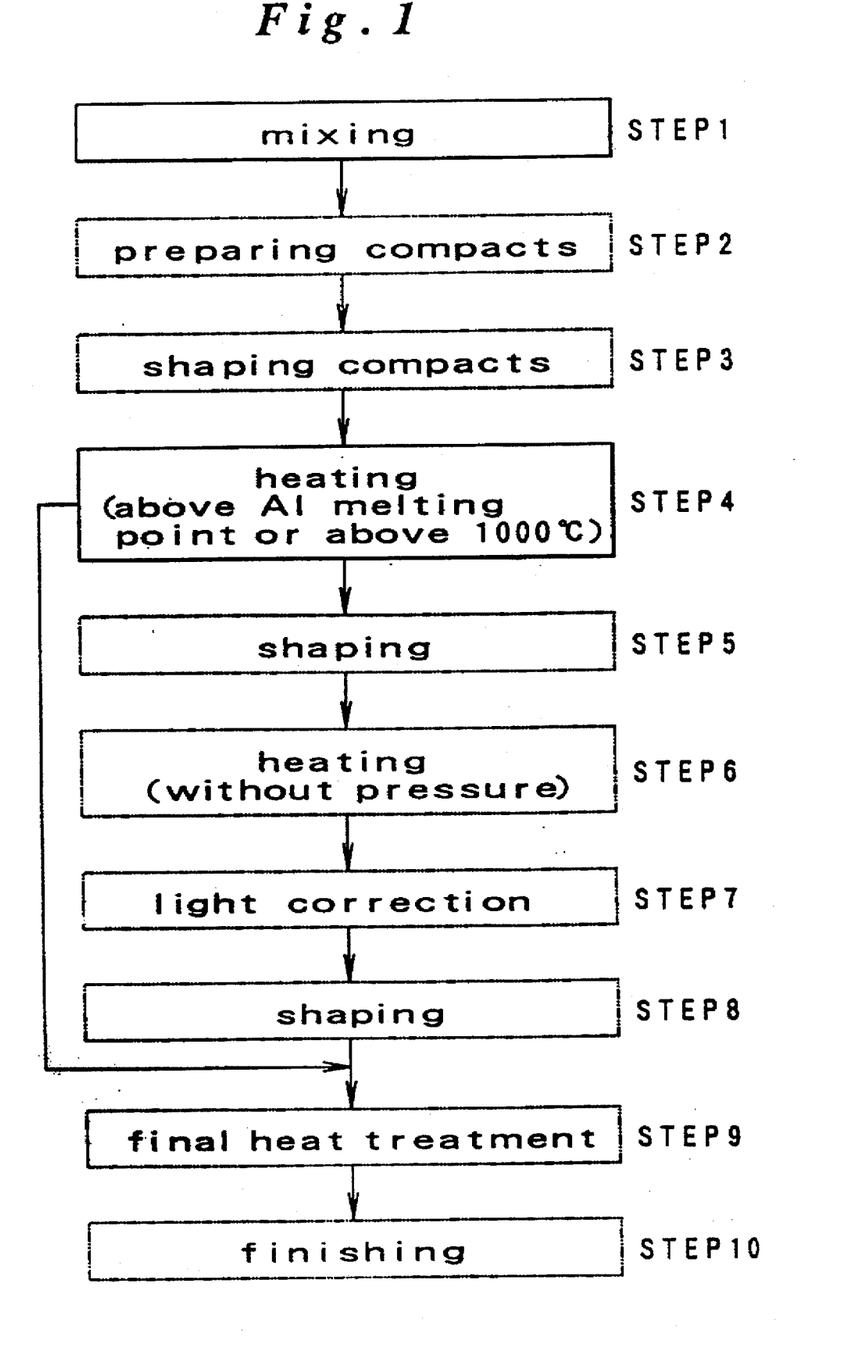
FIG. 1 is a flow chart showing an embodiment of the method of the present invention.

FIG. 1 shows the various steps of an embodiment of the method of present invention. The steps indicated by solid line blocks are essential steps for carrying out the present invention while the steps indicated by chain-dot line blocks are non-essential steps which may be omitted depending on the circumstance.

EXAMPLE 1

In step 1, Ti or a Ti alloy was mixed with Al or an Al alloy at an appropriate composition ratio suitable for forming a desired Ti—Al intermetallic compound. It is also possible to mix two or more Ti—Al intermetallic compounds having different compositions (such as TiAl and Ti₃Al) in the form of powder. Alternatively, a mixture of Ti and Al may be mixed with a Ti—Al intermetallic compound. As a matter of fact, the mixture may consist of an arbitrary combination of Ti, Ti alloys, Al, Al alloys, and Ti—Al intermetallic compounds.

The starting material for carrying out the method of the present invention may preferably be in the form of powder, foil, or filament, but may take other forms. The mixing process may consist of literally mixing a material consisting of two or more components so as to distribute them evenly among themselves, and the material may include a same component in two or more different forms. When the components are in the form of foil, layers of foil of different components may be interleaved as required.

In this embodiment, Al powder and sponge Ti powder both finer than 350 mesh and prepared by the gas atomizer process were mixed together at the weight ratio of Ti:Al= 65.8%:34.2% in a dry ball mill purged by Ar gas in step 1.

The mixture thus prepared in step 1 was formed into a block of compressed powder or a compact in step 2 by applying pressure by using an extruder, a metallic die press, a hot press, a HIP machine, a CIP machine or the like, and, if necessary, the compact was formed into a desired shape in step 3 by forging, machining or the like.

For instance, in step 2, the material mixture was filled into a stainless steel tube, and compressed into a desired shape by carrying out a rotary swaging process on the stainless steel tube. Then, in step 3, this compressed mixture was formed by machining into a cylindrical block 8 mm in diameter and 40 mm in length.

According to an example where steps 2 and 3 are omitted, the mixture prepared in step 1 may be filled into a die mold, and both heat and pressure are applied to the mixture in a hot press or the like in step 4. Alternatively, the mixture may be filled into a capsule to carry out a HIP thereon.

In step 4, the mixture was pressured to 350 kgf/cm² by a quasi HIP in the temperature range of 600° C. to 1300° C., and was held for a certain time period at each of the temperatures. In step 4, it is preferable to heat and press the mixture by a hot press, a HIP or a quasi HIP. In the samples listed in Table 1, sample #2, 3, 5, 6, 8, 9, 11, 12, 14, 15, 17, 18, and 20 were subjected to the heat treatment process of step 6 after carrying out the heating process of step 4.

In step 4, after the mixture was held for a predetermined time period at a prescribed temperature condition in vacuum for each of the samples as shown in Table 1, it was cooled to the room temperature. Samples #1, 2 and 3 were held at 600° C. for six hours, samples #10 to 20 were held in the range of 900° C. to 1200° C. for one hour, and samples #21 was held at a temperature higher than 1200° C. for two hours. Samples #4 to 9 were held at 750° C. for one hour in some cases and six hours in other cases, but the duration of the heating process did not cause any appreciable difference in porosity.

The workability of the mixture may improve if the molding process of step 5 was carried out on the mixture following the heating process of step 4 and before the heat treatment process of step 6. More specifically, the inventors discovered that the workability indeed improved when the heating process of step 4 created a structure in which the α₂ phase is distributed in the γ phase like islands. Furthermore, the molding process of step 5 offers the benefits of collapsing voids left from the heating process of step 4, and adjusting the structure of the work. In one embodiment, the heating process of step 4 is carried out so as to obtain a structure in which a α2 phase is distributed like islands in a matrix of a γ phase, and the molding step is carried out on this structure, the heat treatment step being carried out so as to obtain a lamella structure. It is also possible to carry out the molding process and the heat treatment of steps 5 and 6 simultaneously.

Thus, even when the porosity of the work after the completion of the heating process of step 4 is greater than desired, the porosity may be suitably adjusted by carrying out the molding process of step 5 or the heat treatment process of step 6.

A desired porosity can be also obtained by sintering the mixture of Ti powder and Al powder in step 4 through self-propagating high temperature synthesis without involving sudden heating, and then subjecting it to the molding process of step 5 or the heat treatment process of step 6.

Alternatively, a desired porosity can be obtained by preparing a mixture of TiAl powder and Ti₃Al powder or a mixture containing them, and subjecting it to the heating process of step 4. In this case also, an even better result may be obtained by further carrying out the molding process of step 5 or the heat treatment of step 6.

In the heat treatment process of step 6, two samples of the work were heated to 1200° C. and 1300° C., respectively, in Ar gas flow at near the atmospheric temperature (1.5 atm, for instance), and held at these temperature for two hours before they were cooled. The samples which were heated to the temperature in excess of 1300° C. demonstrated similar favorable properties.

The samples listed in Table 1 were subjected to the heat treatment of step 6 at 1200° C. and 1300° C. for two hours in flowing Ar gas. Substantially the same results were obtained also when they were subjected to 1350° C. for two hours in vacuum. The temperature may be higher than 1350° C., and better results were obtained when the heat treatment was carried out in vacuum than in the atmosphere.

The heat treatment process of step 6 is desired to be carried out without substantially pressurizing the work in view of cost reduction. A primary purpose of this heat treatment process of step 6 is the elimination of voids that were left from the heating process of step 4, by diffusion. A secondary purpose of this heat treatment process is the adjustment of the structure resulted from the heating process of step 4. For instance, the adjustment of the structure consists of a diffusion process for uniformly distributing the components within the work, a heat treatment for adjusting the grain size of the crystals, a heat treatment for recrystallization, and a heat treatment for adjusting the structure through phase changes.

If the molded work is slightly warped or otherwise deformed, a light correction process of step 7 is performed on the work. This correction process typically consists of placing a weight on the work, and can be therefore carried out simultaneously as the heat treatment process of step 6. In the molding process of step 8 following the heat treatment process, a final working process such as forging, machining or the like is carried out. In the last heat treatment process of step 9, a heat treatment such as a precipitation hardening is carried out on the work given with the final shape. The finishing process of step 10 typically consists of shot-peening, grinding or the like.

TABLE 1

| sample number # | pressing temperature (°C.) | hold time (hours) | temperature for heat treatment (°C.) | bending strength (kgf/mm²) | structure | porosity (%) | grade |
| --- | --- | --- | --- | --- | --- | --- | --- |
| 1  | 600  | 6 | none | broken* | B | 6.2 | bad  |
| 2  | 600  | 6 | 1200 | 49.9    | A | 7.2 | bad  |
| 3  | 600  | 6 | 1300 | 54.5    | A | 5.7 | bad  |
| 4  | 600  | 1 | none | broken* | B | 5.7 | bad  |
| 5  | 750  | 1 | 1200 | 66.6    | A | 3.4 | good |
| 6  | 750  | 1 | 1300 | 67.3    | A | 2.6 | good |
| 7  | 750  | 6 | none | broken* | B | 5.7 | bad  |
| 8  | 750  | 6 | 1200 | 60.5    | A | 3.4 | good |
| 9  | 750  | 6 | 1300 | 64.7    | A | 2.8 | good |
| 10 | 900  | 1 | none | broken* | B | 3.9 | bad  |
| 11 | 900  | 1 | 1200 | 76.4    | A | 2.2 | good |
| 12 | 900  | 1 | 1300 | 65.5    | A | 1.8 | good |
| 13 | 1000 | 1 | none | 63.0    | A | 2.2 | good |
| 14 | 1000 | 1 | 1200 | 76.2    | A | 1.8 | good |
| 15 | 1000 | 1 | 1300 | 67.2    | A | 1.3 | good |
| 16 | 1000 | 1 | none | 86.7    | A | 0.3 | good |
| 17 | 1100 | 1 | 1200 | 79.9    | A | 0.3 | good |
| 18 | 1100 | 1 | 1300 | 67.3    | A | 0.3 | good |
| 19 | 1200 | 1 | none | 78.3    | A | 0.2 | good |
| 20 | 1200 | 1 | 1300 | 66.9    | A | 0.3 | good |
| 21 | 1300 | 2 | none | 67.4    | A | 0.3 | good |

*broken before test
A - TiAl + $Ti_3Al$
B - structure other than A is mixed

Figure 2:
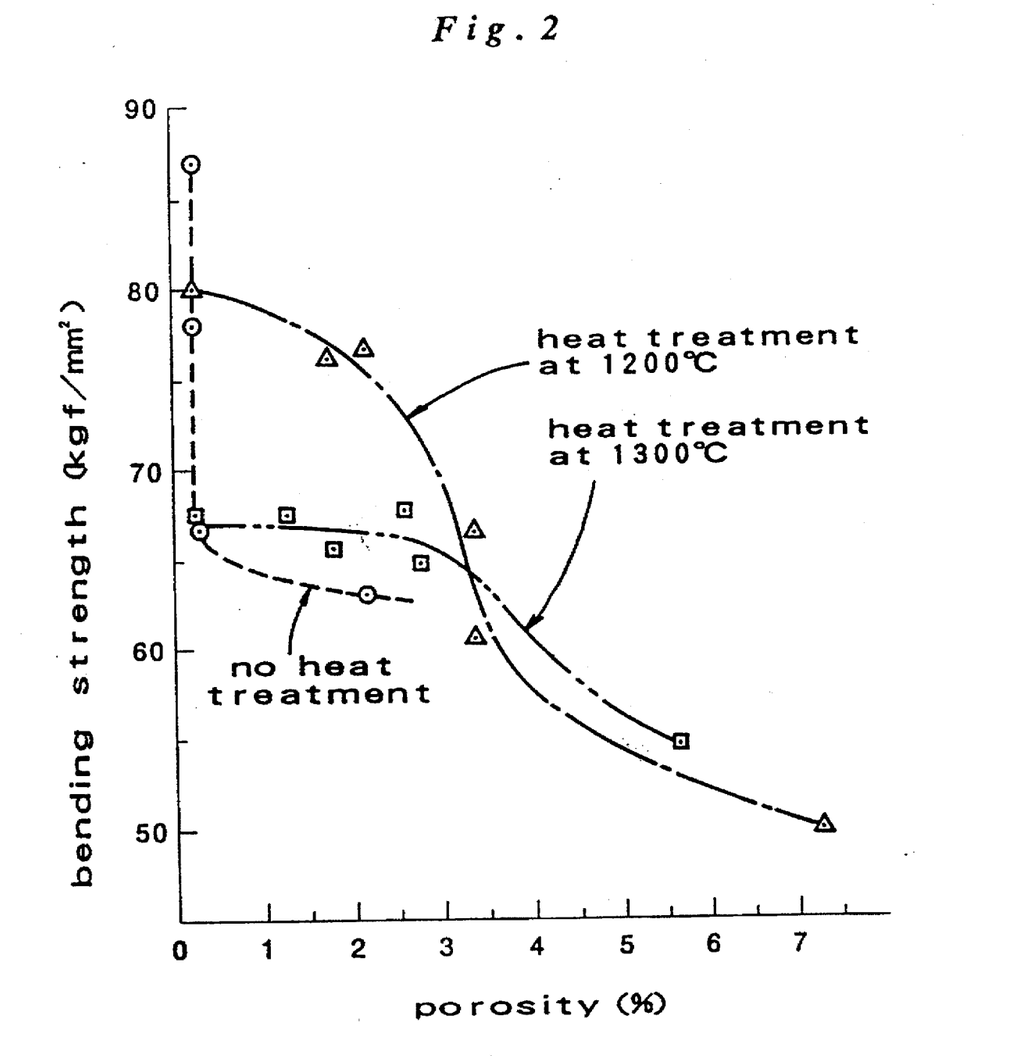
FIG. 2 is a graph showing the relationship between the volume ratio of voids and bending strength.
Figure 3:
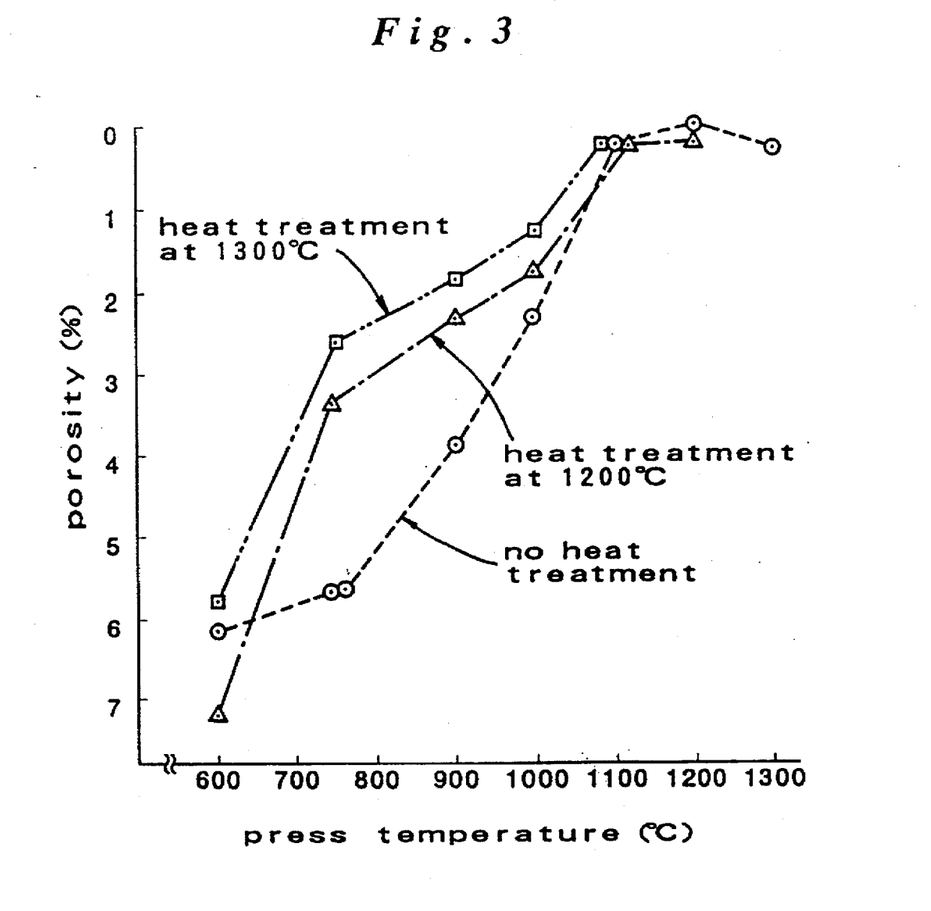
FIG. 3 is a graph showing the relationship between the temperature for the heating process and the volume ratio of voids.
Figure 4:
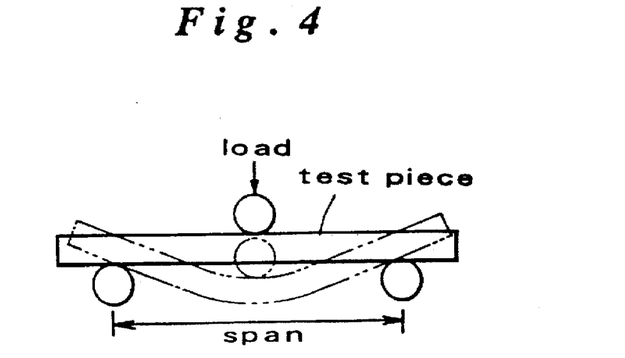
FIG. 4 is a diagram showing the principle of the bending test.

FIG. 2 shows the relationship between the volume ratio of voids and bending strength for each of the samples in Table 1. FIG. 3 shows the relationship between the pressing temperature (temperature in the heating process of step 4) and the volume ratio of voids again for each of the samples in Table 1. The volume ratio of voids or the porosity was obtained by measuring the specific weight by the Archimedean principle, and observing the polished surface of a cross section of the work. The bending strength was obtained by testing a test piece consisting of a rod having a rectangular cross section (3 mm×4 mm×38 mm) on a three-point bending test machine having a span of 30 mm in room temperature as fracture strength as illustrated in FIG. 4.

In terms of reducing the volume of voids or reducing the porosity, it is desired to carry out the heat treatment process of step 6 at a temperature higher than the one used in the heating process of step 4. However, by holding the work in the heat treatment process of step 6 for a long time at a temperature below the one used in the heating process of step 4, an effective heat treatment based on diffusion can be achieved. In particular, when the heating process of step 4 is carried out at a temperature higher than 1000° C., the porosity is reduced to a sufficiently low level, and the temperature for the subsequent heat treatment process of step 6 may therefore be below the temperature for the heating process of step 4. It should be noted, however, that the temperature for obtaining a required structure must be considered separately from that for obtaining a desired porosity. Obviously, the temperature for the heat treatment is preferred to be higher than the temperature at which the final product is going to be used.

As shown in Table 1 and FIG. 2, the bending strength changes significantly near the porosity level of 3.5%, and is relatively great when the porosity is less than 3.5%. The pressing temperature is required to be higher than 1100° C. when the porosity is to be reduced to 0 to 0.3%. However, if the porosity may be in the range of 0.4 to 3.5%, the sintering process may be carried out at temperatures below 1100° C. so that the fabrication facilities may be simplified, and, yet, the desired high mechanical strength can be obtained. In particular, if the range of porosity is selected in a 1.3% to 3.5% range, the pressing temperature may be reduced to 1000° C., and the fabrication facilities can be extremely simplified.

In all of the samples in Table 1 which were subjected to the bending test, the porosity was substantially low, and the voids were distributed evenly within each sample. The average diameter of the voids was less than 15 μm, and the diameters of most of the voids were in the 5 to 15 μm range, with almost no voids having diameters greater than 50 μm. The porosity ranged between 0.2% to 7.2%, and this has a strong correlation with the numbers of voids in the 5 to 15 μm range.

Thus, reducing the volume ratio of voids below 3.5% and the average diameter of voids below 15 μm was highly effective in obtaining an article of high mechanical strength. Reducing the diameters of voids to be below 50 μm is also effective in achieving the same goal. The use of the materials in the form of powder is effective in finely and evenly distributing voids throughout the work. The use of reaction sintering was also effective in finely and evenly distributing voids throughout the work.

When the heating process of step 4 was carried at temperatures higher than 1100° C. as samples #16 to 21 in Table 1, the molded work had a density approximately equal to the full density of the material (100% density). By thus reducing the volume ratio of voids below 0.5%, the number of voids can be reduced to an extremely small number, and the reliability of the mechanical strength can be improved to the level of that of a molded article consisting of purely solid equivalent material.

This may be explained by the fact that the mechanical strength of the molded article sharply drops when it is heated beyond 1100° C. Samples #17, 18 and 20 were subjected to the heating process of step 4 at temperatures higher than 1100° C., and then subjected to the heat treatment process of step 6 at even higher temperatures, but the reduction in the porosity was not substantial as that of samples #16, 19 and 21 which were not subjected to the heat treatment process of step 6. Also, it was observed that the use of temperatures higher than 1100° C. for the heating process of step 4 sometimes did not cause any appreciable reduction in the porosity (or, in other words, any increase in the relative density).

When no heat treatment of step 6 was carried as was the case with samples #1, 4, 7, 10, 13, 16, 19 and 21, and the heating process of step 4 was carried out at temperatures below 900° C. as was the case with samples #1, 4, 7 and 10, the volume ratio of voids was relatively high and the structure included components other than (TiAl+Ti3Al). More specifically, the structure included (TiAl+Ti$_3$Al), but the metallic Ti phase was conspicuously remaining, and Al$_3$Ti was also present. As the pressing temperature in the heating process of step 4 was increased, the metallic γ phase and Al$_3$Ti were converted into (TiAl+Ti$_3$Al) by diffusion, and were entirely converted into (TiAl+Ti$_3$Al) when the pressing temperature was increased over 1000° C.

As discussed above, those samples, for which the pressing temperature was below 900° C., and no heat treatment of step 6 was carried out, had highly uneven structures, and their mechanical strengths were so low that they developed cracks and chippings when they were worked into test pieces for bending tests, and could not be even tested of their mechanical strengths. In other words, such uniform structures are not suitable for accomplishing the objects of the present invention.

Figure 5:
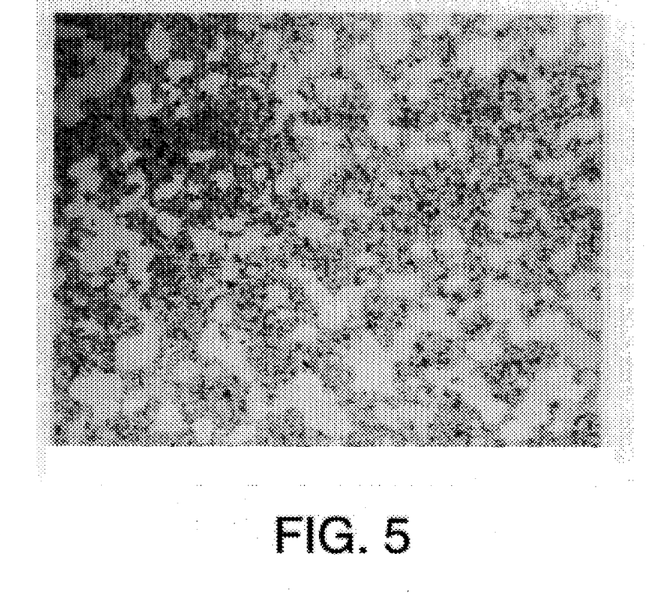
FIG. 5 is a microscopic photograph (at the magnification factor of 100) of the metallic structure of the intermetallic compound which was prepared by the method of the present invention.

On the other hand, even when the pressing temperature was below 900° C., those samples which were subjected to the heat treatment process of step 6 at 1200° C. for two hours in flowing Ar gas had structures including crystal formations consisting mainly of TiAl (γ phase) and crystal formations consisting mainly of Ti$_3$Al (α$_2$ phase) as shown in the photograph of FIG. 5. The white parts shown in this photograph are Ti$_3$Al particles, and the dark parts consist of TiAl.

Figure 6:
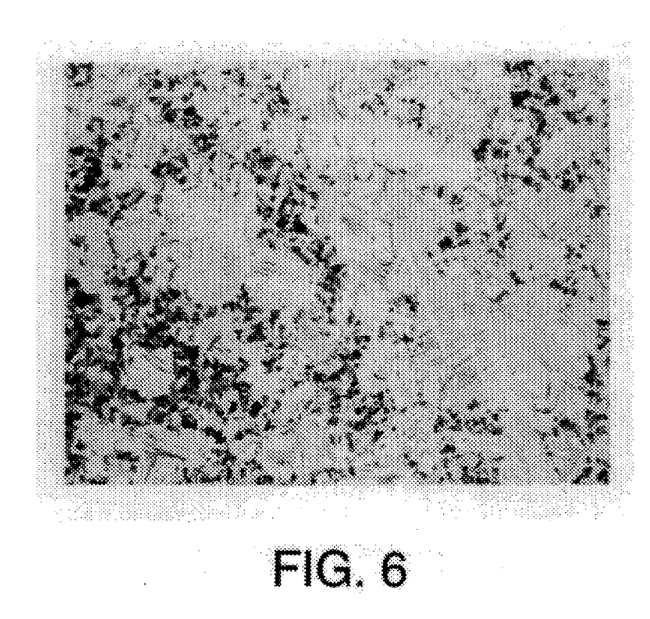
FIG. 6 is a microscopic photograph (at the magnification factor of 100) of the metallic structure of the intermetallic compound which was prepared by the method of the present invention, after the heat treatment is carried out.

The structure resulting from two hours of the heat treatment process of step 6 at the temperature of 1300° C. in flowing Ar gas consisted of a layered or lamella structure or alternating layers of the phase consisting primarily of TiAl and the phase consisting of Ti$_3$Al as shown in the photograph of FIG. 6. This lamella structure is shown as the striped pattern in this photograph, and this structure improves the heat resistance of the material.

As discussed above, the tendency shown in the graph of FIG. 2 (that the mechanical strength improves when the porosity is less than 3.5%) holds true equally for the structure including the γ phase in a significant proportion shown in the photograph of FIG. 5 (1200° C., two hours), and for the structure including the lamella structure in a significant proportion shown in the photograph of FIG. 6 (1300° C., two hours). As a matter of fact, it appears according to the results of our experiments that this tendency is applicable without regard to the structure, and appears to be a common tendency at least for most Ti—Al intermetallic compounds consisting of TiAl+Ti$_3$Al.

The inventors have also discovered that the structure including an island-like distribution of the α$_2$ phase in the γ phase as shown in the photograph of FIG. 5 improves the workability. Specifically, whereas the conventional Ti—Al intermetallic compounds had such poor workability that some measures were necessary to make them usable, such as reducing the size of crystals (15 μm) and working the material at temperatures higher than 1000° C., the structure shown in the photograph of FIG. 5 allows the material to have a favorable workability combined with the possibility of further improvement of the material properties by collapsing the voids remaining in the structure. This structure can be easily obtained by the reaction synthesis method.

Table 2 shows the results of load tests obtained by measuring the maximum loads with regard to samples subjected to the quasi HIP in the temperature range of 1100° C. to 1200° C. in the heating process of step 4, and worked in the temperature range of 800° C. to 1000° C. The working process was carried out by a three-point bending test machine as illustrated in FIG. 4, and the maximum load is given as the load at the time when a prescribed bending deflection has occurred.

TABLE 2

| sample number # | pressing temperature (°C.) | max. load (kgf) | fracture | max. load after heat treatment (kgf) | quasi HIP temperature (°C.) | grade |
| --- | --- | --- | --- | --- | --- | --- |
| 31 | 800 | 56 | none | NA | 1100 | good |
| 32 | 800 | 58 | none | NA | 1100 | good |
| 33 | 800 | 60 | yes | broken | 1350 | bad |
| 34 | 800 | 68 | yes | broken | 1350 | bad |
| 35 | 900 | 33 | none | 51 | 1100 | good |
| 36 | 900 | 53 | none | NA | 1350 | bad |
| 37 | 900 | 49 | none | NA | 1350 | bad |
| 38 | 1000 | 17 | none | NA | 1100 | good |
| 39 | 1000 | 28 | none | NA | 1350 | bad |

As shown in Table 2, samples #33 and 34 (samples for comparison) ruptured when they were subjected to a plastic working process at 800° C., but samples #31 and 32 (including an island-like distribution of the α$_2$ phase in the γ phase) did not rupture by the same plastic working process, and required less load for the same working process. In other words, it was verified that the structure shown in the photograph of FIG. 5 provides a favorable workability. When the plastic working process was carried out at 900° C. and 1000° C., both groups of samples #35 and 38 (including an island-like distribution of the α$_2$ phase in the γ phase) and samples #36, 37 and 39 (samples for comparison), the first group of samples or samples #35 and 38 (the present invention) required a far less load for working, or, in other words, are far more workable than the second group of samples.

Sample #35 in Table 2 was subjected to a plastic working in the molding process of step 5 following the process of heat treatment, and then to the heat treatment of step 6. The resulting structure was similar to that shown in the photograph of FIG. 6 (the structure including a lamella structure). This sample was then polished, and was further subjected to a bending. It was observed that the maximum load was increased to 51 kgf/cm$^2$, and the resistance to heat was improved. The molding process included in the above embodiment is advantageous in improving the workability of the intermetallic compound having the range of composition prone to the creation of a lamella structure which provides a high level of resistance to heat but a poor workability.

A light-weight and heat-resistant pin (8.5 mm in diameter and 70 mm in length) was fabricated by using an intermetallic compound according to the method of the present invention. A quasi HIP was carried out as the heating process of step 4 at the temperature of 1100° C. for two hours in vacuum environment, and a heat treatment for diffusion was carried out as the heat treatment process of step 6 at 1300° C. for two hours. The slight warping that was created during the heating process of step 4 was corrected by placing a weight on the pin during the heat treatment process of step 6 as a plastic working process. This pin was then machined into a test piece, and demonstrated the tensile strength of 28 kgf/cm$^2$ when a tension test was conducted at the temperature of 900° C. When a similar tension test was conducted on a sample for comparison which was subjected to a quasi HIP at the temperature of 1300° C. for two hours, and then to a plastic working process at the temperature of 1200° C., the tensile strength was 29 kgf/cm$^2$.

The heat treatment process may also be carried out after a plastic working process, and various other plastic working processes may be carried out. Such plastic working processes may include bending, compressing, tensioning, isotropic or isostatic compression, hot forging, super plastic working and so on. The deformation involved in the plastic working process may be significantly large.

As discussed above, by setting the pressing temperature in the heating process of step 4 at a relatively low level, it is possible to reduce the fabrication cost while achieving a mechanical strength comparable to those obtained by using high pressures and high temperatures. The reasons behind this fact are given in the following.

First of all, by lowering the pressing temperature, sintering of alumina in the quasi HIP using alumina can be avoided, and the product can be more easily taken out. Furthermore, reaction with alumina can be controlled, and the surface texture of the molded product can be improved. For instance, the light-weight and heat resistant pin mentioned above is preferred to have a smooth surface texture so that the subsequent machining process may be omitted, and the fabrication cost may be thereby reduced. Even when machining is required, a smooth surface texture requires less machining, and it also can reduce the fabrication cost.

It is preferable if a sufficiently solid molded work could be obtained simply by heating it without pressing. However, in reality, simply heating the mixture of Ti and Al powders or the like can only achieve a 70% density, and pressing is normally necessary. The pressing temperature is desired to be low because heating the work to a high temperature during pressing requires expensive facilities. The need for pressing the work increases the fabrication cost, and so does the need for heating the work during pressing. Normally, the higher the pressing temperature, the higher the fabrication cost becomes. Facilities and equipment made of heat resistant materials tend to be more expensive than those with limited heat resisting capabilities. Furthermore, a higher pressing temperature means a longer time for heating the work to the pressing temperature. All these factors indicate less fabrication cost as the pressing temperature is lowered. In particular, it is desirable in terms of cost to restrict the upper limit of the pressing temperature below 1250° C.

EXAMPLE 2

Four kinds of compacts were prepared by changing the mixing ratio of Ti powder and Al powder so that the compositions as given by samples 41 to 44 in Table 3 may be obtained. Four sets of test pieces were obtained from these samples by placing each sample under pressure by a quasi HIP using alumina powder, heating it to 1350° C., holding it at this temperature for two hours, and cooling it to the room temperature by using gas. These test pieces were then subjected to the mechanical strength test using a three-point bending test machine as shown in FIG. 4.

TABLE 3

| sample number # | composition (at % Al) | phase | structure | evenness | porosity (vol %) | strength at room temp. (kgf/mm$^2$) | strength at 800° C. (kgf/mm$^2$) |
| --- | --- | --- | --- | --- | --- | --- | --- |
| 41 | 46 | α | lamella | A* | 0.2 | 101 | 104 |
| 42 | 48 | α + γ | lamella + γ | B* | 0.3 | 61 | 85 |
| 43 | 50 | α + γ | lamella + γ | B* | 0.3 | 67 | 84 |
| 44 | 52 | γ | lamella + γ | B* | 0.3 | 73 | 70 |

A*: uniform lamella structure (more than 97 vol %)
B*: random mixture of lamella and γ

Figure 7:
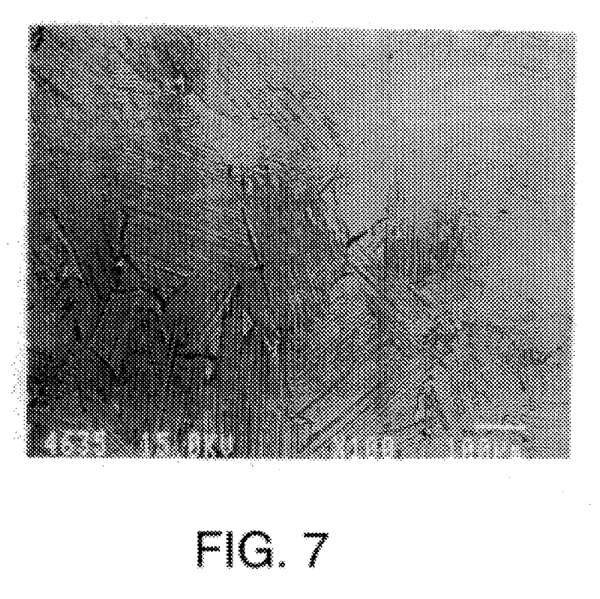
FIG. 7 is a microscopic photograph (at the magnification factor of 75) of the uniform lamella structure of the intermetallic compound obtained by the method of the present invention.
Figure 8:
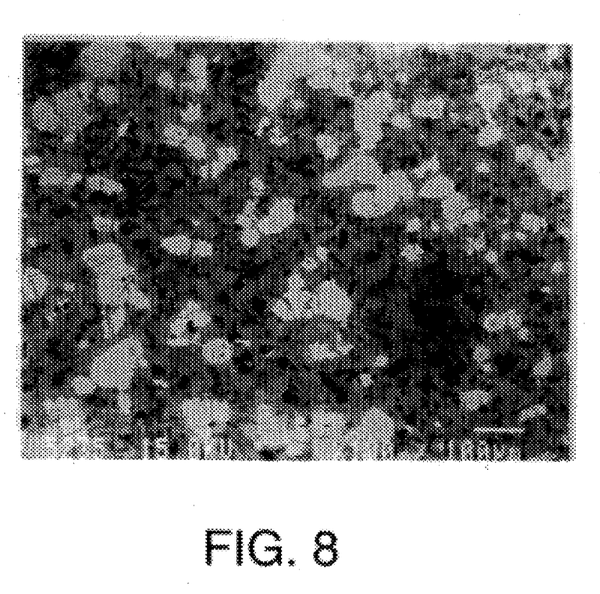
FIG. 8 is a microscopic photograph (at the magnification factor of 75) of the structure of the intermetallic compound including a mixture of a lamella structure and τ.

The equilibrium phase diagram for each of the samples at the temperature of 1350° C. shows the single α phase for sample #41 containing 46$_{at}$% of Al, and the single γ phase for sample #44 containing 52$_{at}$% of Al. Therefore, it was expected that a uniform structure should be obtained in either case. However, in reality, a uniform structure was obtained only from sample #41, and not from sample #44. The structures of samples 41 and 44 are shown in the photographs of FIGS. 7 and 8, respectively, which are both reflection electron beam microscopic composition images. A reflection electron beam microscopic composition image is based on a special form of electron microscopic imaging technique, and aids the observation of the composition by showing heavier elements as white areas and lighter elements as darker areas. In FIG. 8, the dark or gray areas are the γ phase, and the white stripes are the lamella structure which is distributed in the γ phase.

Sample #41 having the uniform structure was determined to have the highest mechanical strength from the room temperature to high temperatures. It may be attributed to the fact that the delay in the homogenization of the structure in which the α phase is distributed in the γ phase as can be surmised from the photograph of FIG. 8. By studying the speed of homogenization at a same temperature, it was found that the change from α+γ to α is substantially faster than the change from γ+α to γ. It shows that it is preferable to cause diffusion by a heat treatment in the α phase to the end of obtaining a uniform structure, and it also provides a structure having a high mechanical strength.

EXAMPLE 3

Figure 9:
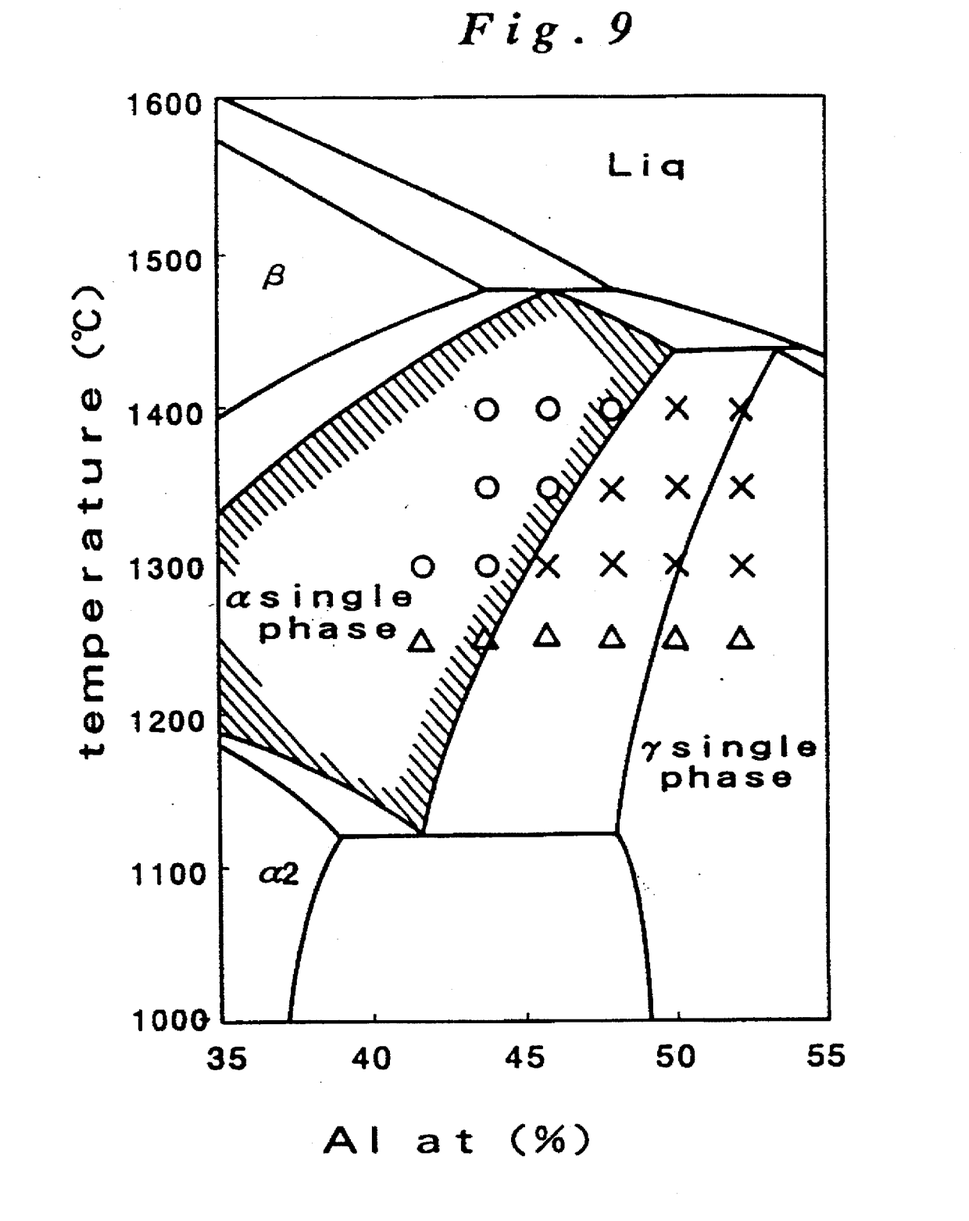
FIG. 9 is an equilibrium phase diagram of a Ti—Al intermetallic compound.

Compacts of Ti and Al powders adjusted to contain six different amounts of Al (42 to $52_{at}\%$) as listed in Table 4 were heated to a temperature higher than 1100° C. while being pressurized by a quasi HIP, and heated for sintering before they were finally cooled to the room temperature by gas. Thereafter, they were subjected to the diffusion heat treatment by being held at four different temperatures for two hours as listed in Table 4, and the obtained structures were studied. The results obtained from Table 4 were then plotted in a Ti—Al equilibrium phase diagram as shown in FIG. 9. The porosity was less than 0.5% in all of the samples.

TABLE 4

|  | 42 at % Al | #44 | #46 | #48 | #50 | #52 |
|---|---|---|---|---|---|---|
| 1400° C. | NA | A* | A* | A* | B* | B* |
| 1350° C. | NA | A* | A* | B* | B* | B* |
| 1300° C. | A* | A* | B* | B* | B* | B* |
| 1250° C. | C* | C* | C* | C* | C* | C* |
|  | (porosity was less than 0.5% in all the cases) | | | | | |

A*: uniform lamella structure (more than 97 vol %)
B*: random mixture of lamella and γ
C*: insufficient diffusion, mixture of lamella + γ + equiaxial $\alpha_2$ granules It was determined from Table 4 and FIG. 9 that a uniform lamella structure can be obtained by carrying out the diffusion heat treatment in the α phase region, and the resulting porosity was sufficiently low. It was also found that a uniform structure can be easily obtained by using a temperature higher than 1250° C. for the heat treatment. A sample of 42at% Al using 1250° C. for its heat treatment indicated that the heat treatment may not ensure a uniform structure even in the α phase region if the temperature is too low. Even in such a case, by maintaining the temperature for the heat treatment for a sufficient period time, a desired uniformity can be obtained. If the speed of cooling following the heat treatment is too slow, a uniform lamella structure may not be obtained. It is therefore desirable to set the speed of cooling from the α phase region greater than 1° C./min.

Above described method is highly effective when the reaction synthesis process is employed, and is particularly effective in achieving a uniform structure when Ti—Al alloy powder is used for the material, and when the conventional processes such as the melting process and the forging process are used.

EXAMPLE 4

In the same manner as Examples 1 and 2, a mixture of Ti and Al powders were subjected to the reaction synthesis process in which the compact was pressurized and heated by the quasi HIP, and a rod 6.2 mm in diameter and 10 mm in length was obtained. It contained 48at% of Al, and the $\alpha_2$ phase was distributed in the matrix of the γ phase in its structure which was similar to that of FIG. 5. It was then compressed at 900° C. until its length was reduced to 5 mm, and a lamella structure was grown by subjecting it to a heat treatment in flowing Ar gas. It was further compressed to the length of 3 mm at 900° C., and its mechanical strength was measured as given in Table 5.

TABLE 5

| Sample # | heat treatment after compression (°C.) | obtained structure | strength (kgf/mm²) |
|---|---|---|---|
| 51 | NA | $\gamma + \alpha_2$ | 26 |
| 52 | 1350 | lamella + γ | 38 |
| 53 | 1400 | lamella | 41 |

Figure 10:
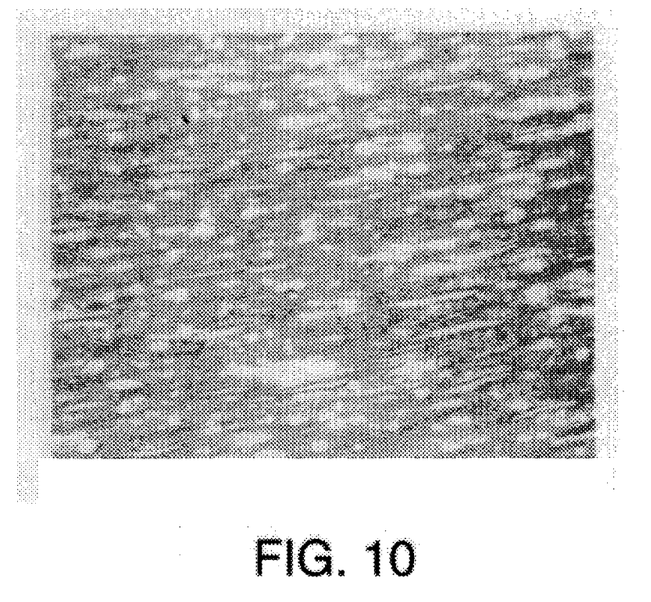
FIG. 10 is a microscopic photograph (at the magnification factor of 100) of the metallic structure of τ+$\alpha_2$ after compression.
Figure 11:
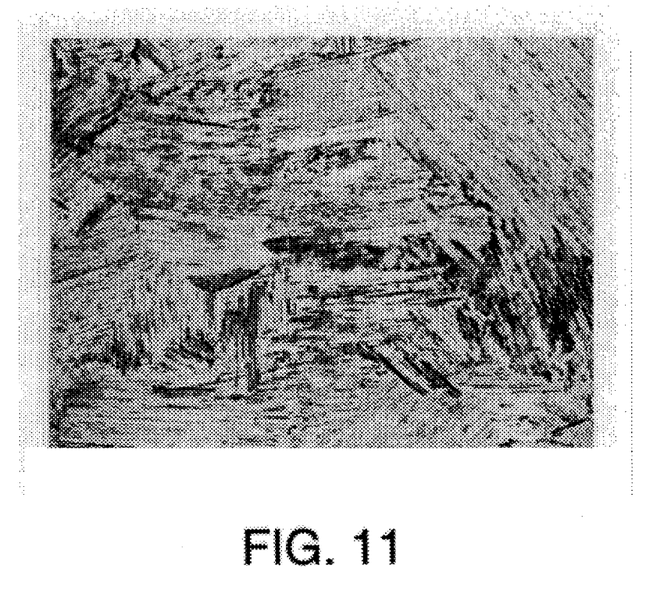
FIG. 11 is a microscopic photograph (at the magnification factor of 100) of the metallic structure of the lamella structure after compression and a subsequent heat treatment.

FIG. 10 is a microscopic image of a structure which is not subjected to a heat treatment following the above described compression process (sample 51 of Table 5). The vertical direction coincides with the direction of compression. FIG. 11 is a microscopic image of a structure which is subjected to a heat treatment at 1400° C. following the above described compression process (sample #53 of Table 5). These microscopic images were obtained by using an optical microscope, and the white parts are the $\alpha_2$ phase ($Ti_3Al$) while the dark parts are the γ phase (TiAl).

In the photograph of FIG. 10, the crystal grains were made finer by the compression, and the size of the crystals showed some correlation with the degree of deformation. Based on this finding, it was anticipated that the history of the compression would remain even after the heat treatment for homogeneity was carried out. But, in reality, it was found that the history of the compression did not remain when the heat treatment was conducted following the compression process, due to significant changes caused in the phase (sample #53, for instance). When the history of compression remained, it would cause some unevenness in the structure, and the fine crystal structure has a tendency to diminish the resistance to heat.

The structure of FIG. 11 (sample #53) demonstrated a uniform lamella structure free from the history of compression because the heat treatment was carried out in the α single phase region. It was feared that the porosity may be substantially high due to the creation of defects during the compression process even in spite of the subsequent diffusion heat treatment, but, in reality, the porosity did not increase at all.

To evaluate the deformation capability of the sample, a sample was prepared in the same way as described above and having the same size (6.2 mm in diameter, and 10 mm in length), and generation of cracks was visually observed as it was compressed to 3.5 mm at the rate of 0.5 mm/min at 800° C. The results are summarized in Table 6.

TABLE 6

| Sample # | heat treatment for diffusion (°C.) | obtained structure | cracks |
|---|---|---|---|
| 61 | NA | $\gamma + \alpha_2$ | no |
| 62 | 1350 | lamella + γ | yes |
| 63 | 1400 | lamella | yes |

It shows that the ($\gamma+\alpha_2$) structure has a favorably workability. In other words, a favorable heat resistance can be obtained by working the sample when it consists of a highly workable structure, and then subjecting it to a heat treatment. Thus, a fabrication method is provided which can improve workability without impairing the performance of the material as a heat-resistant, light-weight material.

The workable structure ($\gamma+\alpha_2$) mentioned in this disclosure is able to retain its desirable property even when it contains small amounts of a lamella structure, Ti, and Al$_3$Ti. α$_2$ changes into α (a solid solution of Ti) at a temperature higher than 1200° C., and the resistance against working is reduced even further. Therefore, an even better workability can be obtained in this phase.

The workable (γ+α$_2$) structure can be obtained by carrying out the sintering heating process and the diffusion heat treatment in the temperature range of 1000° to 1250° C. when the reaction synthesis process was employed. When the temperature is lower than 1000° C., other intermetallic compounds such as Al$_3$Ti tend to be formed. When the temperature is higher than 1250° C., a lamella structure may be excessively formed, and it will impair the workability of the material.

The present invention is effective in increasing the mechanical strength of intermetallic compounds including TiAl, Ti$_3$Al and/or (TiAl+Ti$_3$Al), but may be applicable to other Ti—Al intermetallic compounds. It is also anticipated that various properties may be improved by adding suitable amounts of various elements such as Si, Nb, Mn, Cr, V or the like, various compounds such as TiB$_2$, Y$_2$O$_3$, Ti$_5$Si$_3$, ceramics, intermetallic compounds or the like.

Thus according to the present invention, the mechanical strength of articles made of Ti—Al intermetallic compounds can be improved, and the fabrication costs can be reduced because the fabrication process according to the present invention involves only relatively low temperatures when pressing and heating the sample at the same time. The mechanical strength of an article according to the present invention is not only improved but is highly predictable, or, in other word, highly reliable. Furthermore, during the process of fabrication, the work may demonstrate a highly favorable workability so that the final shape can be given to the work without involving any undue difficulty.

Although the present invention has been described in terms of specific embodiments thereof, it is possible to modify and alter details thereof without departing from the spirit of the present invention.

What we claim is:

1. A method for fabricating an article essentially consisting of one or more of Ti—Al intermetallic compounds, comprising the steps of:
    preparing a mixture of a first material in solid form and a second material in solid form, wherein each of said first material and said second material is selected from a group consisting of Ti, Ti alloys, Al, Al alloys, and Ti—Al compounds, such that said mixture has a composition suitable for forming a desired Ti—Al intermetallic compound;
    heating said mixture to form a structure comprising a first phase and a second phase wherein said first phase is distributed like islands in a matrix of said second phase, a plurality of voids being embedded within said structure; and
    conducting diffusion heat treatment to eliminate one or more of said voids such that after said diffusion heat treatment said structure has a volume ratio of said voids to the total volume of said structure ranging between 1.3% and 3.5%.

2. The method according to claim 1, wherein said heating step includes pressing of said mixture while said mixture is heated to a temperature higher than 1000° C.

3. The method according to claim 1, wherein said temperature for said heating step is higher than a temperature for melting an Al metallic phase, and said step of diffusion heat treatment is conducted at a temperature higher than said temperature for said heating step.

4. The method according to claim 1, wherein said diffusion heat treatment step is carried out substantially without applying any pressure to said mixture.

5. The method according to claim 1, wherein a molding step is carried out between said heating step and said diffusion heat treatment step.

6. The method according to claim 1, wherein said heating step is carried out such that said first phase is α2 phase said second phase is γ phase, and a molding step is carried out on said structure at a temperature less than 1,000° C., said diffusion heat treatment step being carried out so as to obtain a lamella structure.

7. The method according to claim 1, wherein said heating step is carried out in an α phase.

8. The method according to claim 7, wherein said heating step involves a temperature higher than 1250° C.

9. The method according to claim 1, wherein said diffusion heat treatment step is carried out in an α phase.

10. The method according to claim 6, wherein said diffusion heat treatment step is carried out in an α phase.

11. The method according to claim 10, wherein said diffusion heat treatment step involves a temperature higher than 1250° C.

12. The method according to claim 1, wherein said heating step includes a pressing of said mixture in a quasi hot isostatic process using a pressing medium consisting of powder or granular material having a heat resistance against said temperature for said heating step.

13. The method of claim 1 wherein said solid form is powder or filament or wire, and said mixing step comprises distributing said first material approximately evenly throughout said second material.

14. The method of claim 1 wherein said solid form is foil, and said mixing step comprises approximately evenly interleaving said second material foils with said first material foils.

15. A method for fabricating an article essentially consisting of one or more Ti—Al intermetallic compounds, comprising the steps of:
    preparing the mixture of a plurality of materials selected from a group consisting of Ti, Ti alloys, Al, Al alloys, and Ti—Al compounds, having a composition suitable for forming a desired Ti—Al intermetallic compound;
    heating said mixture so that said mixture may be sintered; and
    conducting a process of diffusion heat treatment substantially without applying any pressure to said mixture following said heating step to achieve a volume ratio of voids no more than 3.5% of the volume of said mixture.

16. The method according to claim 15, wherein said heating step includes pressing of said mixture while said mixture is heated to a temperature higher than 1000° C.

17. The method according to claim 15, wherein said temperature for said heating step is higher than a temperature for melting an Al metallic phase, and wherein said step of diffusion heat treatment is conducted at a temperature higher than said temperature of said heating step.

18. The method according to claim 15, wherein a molding step is carried out between said heating step and said diffusion heat treatment step.

19. The method according to claim 15, wherein said heating step is carried out in an α phase.

20. The method according to claim 15, wherein said heating step involves a temperature higher than 1250° C.

21. The method according to claim 15, wherein said diffusion heat treatment step is carried out in an α phase.

22. The method according to claim 13, wherein said diffusion heat treatment step involves a temperature higher than 1250° C.

23. A method for fabricating an article comprising the steps of:

preparing a mixture of Ti—Al powder and Ti3Al powder;

heating said mixture at a predetermined temperature for a predetermined time period in vacuum to form a structure having a plurality of voids and α2 phase distributed like islands in a matrix of γ phase; and molding said structure to collapse at least one void left from said heating step such that said structure has a volume ratio of voids ranging between 1.3% and 3.5% of the volume of said structure.

24. The method of claim 23 further comprising conducting diffusion heat treatment to eliminate at least one void left from said heating.

* * * * *